(12) United States Patent  (10) Patent No.: US 9,320,552 B2
Jacene et al.  (45) Date of Patent: Apr. 26, 2016

(54) PASSIVE SCREW LOCKING MECHANISM

(71) Applicant: DePuy Synthes Products, Inc., Raynham, MA (US)

(72) Inventors: Michael Jacene, Blackstone, MA (US); Jonathan Fanger, Raynham, MA (US); John R. Hawkins, Cumberland, RI (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/202,432

(22) Filed: Mar. 10, 2014

(65) Prior Publication Data

US 2014/0188177 A1 Jul. 3, 2014

Related U.S. Application Data

(63) Continuation of application No. 11/691,760, filed on Mar. 27, 2007, now Pat. No. 8,702,762.

(51) Int. Cl.
*A61B 17/80* (2006.01)
*A61B 17/86* (2006.01)

(52) U.S. Cl.
CPC ......... *A61B 17/8047* (2013.01); *A61B 17/8057* (2013.01); *A61B 17/8605* (2013.01)

(58) Field of Classification Search
CPC .................. A61B 17/8047; A61B 17/8605
See application file for complete search history.

(56) References Cited

U.S. PATENT DOCUMENTS

| | | |
|---|---|---|
| 1,177,810 A | 4/1916 | Rogness |
| 3,711,138 A | 1/1973 | Davis |
| 4,943,292 A | 7/1990 | Foux |
| 4,988,351 A | 1/1991 | Paulos et al. |
| 5,053,036 A | 10/1991 | Perren et al. |
| 5,057,111 A | 10/1991 | Park |
| 5,127,914 A | 7/1992 | Calderale et al. |
| 5,151,103 A | 9/1992 | Tepic et al. |
| 5,269,784 A | 12/1993 | Mast |
| 5,364,399 A | 11/1994 | Lowery et al. |
| 5,474,553 A | 12/1995 | Baumgart et al. |

(Continued)

FOREIGN PATENT DOCUMENTS

| | | | |
|---|---|---|---|
| EP | 1348390 A2 | 10/2003 | |
| FR | 2861980 A1 * | 5/2005 | ............. A61B 17/70 |

(Continued)

OTHER PUBLICATIONS

European Office Action for corresponding European Application No. 08730817.7 mailed May 13, 2014.

(Continued)

*Primary Examiner* — Christian Sevilla

(74) *Attorney, Agent, or Firm* — Nutter McClennen & Fish LLP

(57) ABSTRACT

Methods and devices are provided for passively locking a bone screw within a bone plate. In particular, the methods and devices allow a bone screw to be locked within a thru-hole in a bone plate without requiring any additional locking steps. In an exemplary embodiment, an annular feature is provided in a thru-hole of a bone plate, or in a bushing that is disposed within a thru-hole of a bone plate, for engaging a bone screw. The annular feature can be configured such that it allows the bone screw to be inserted through the thru-hole at various insertion angles while still being effective to prevent back-out of the bone screw, thereby locking the screw to the plate.

16 Claims, 6 Drawing Sheets

(56) References Cited

U.S. PATENT DOCUMENTS

| | | |
|---|---|---|
| 5,501,684 A | 3/1996 | Schlapfer et al. |
| 5,520,690 A | 5/1996 | Errico et al. |
| 5,534,027 A | 7/1996 | Hodorek |
| 5,578,034 A | 11/1996 | Estes |
| 5,607,426 A | 3/1997 | Ralph et al. |
| 5,607,428 A | 3/1997 | Lin |
| 5,643,265 A | 7/1997 | Errico et al. |
| 5,735,853 A | 4/1998 | Olerud |
| 5,741,258 A | 4/1998 | Klaue et al. |
| 5,797,912 A | 8/1998 | Runciman et al. |
| 5,810,823 A | 9/1998 | Klaue et al. |
| 5,843,082 A | 12/1998 | Yuan et al. |
| 5,876,402 A | 3/1999 | Errico et al. |
| 5,902,303 A | 5/1999 | Eckhof et al. |
| 5,904,683 A | 5/1999 | Pohndorf et al. |
| 5,931,838 A | 8/1999 | Vito |
| 5,954,722 A | 9/1999 | Bono |
| 6,017,345 A | 1/2000 | Richelsoph |
| 6,030,389 A | 2/2000 | Wagner et al. |
| 6,036,693 A | 3/2000 | Yuan et al. |
| 6,139,550 A | 10/2000 | Michelson |
| 6,193,721 B1 | 2/2001 | Michelson |
| 6,206,882 B1 | 3/2001 | Cohen |
| 6,241,731 B1 * | 6/2001 | Fiz ................................ 606/65 |
| 6,248,108 B1 | 6/2001 | Tormala et al. |
| 6,261,291 B1 | 7/2001 | Talaber et al. |
| 6,273,889 B1 | 8/2001 | Richelsoph |
| 6,322,562 B1 | 11/2001 | Wolter et al. |
| 6,383,186 B1 | 5/2002 | Michelson |
| 6,383,187 B2 | 5/2002 | Tormala et al. |
| 6,398,783 B1 | 6/2002 | Michelson |
| 6,402,756 B1 | 6/2002 | Ralph et al. |
| 6,416,528 B1 | 7/2002 | Michelson |
| 6,428,542 B1 | 8/2002 | Michelson |
| 6,454,769 B2 | 9/2002 | Wagner et al. |
| 6,454,771 B1 | 9/2002 | Michelson |
| 6,527,776 B1 | 3/2003 | Michelson |
| 6,575,975 B2 | 6/2003 | Brace et al. |
| 6,592,586 B1 | 7/2003 | Michelson |
| 6,599,290 B2 | 7/2003 | Bailey et al. |
| 6,602,255 B1 | 8/2003 | Campbell et al. |
| 6,620,163 B1 | 9/2003 | Michelson |
| 6,661,666 B1 | 12/2003 | Dauksher |
| 6,712,818 B1 | 3/2004 | Michelson |
| 6,780,186 B2 | 8/2004 | Errico et al. |
| 6,890,334 B2 | 5/2005 | Brace et al. |
| 6,916,320 B2 | 7/2005 | Michelson |
| 6,926,718 B1 | 8/2005 | Michelson |
| 6,936,050 B2 | 8/2005 | Michelson |
| 6,936,051 B2 | 8/2005 | Michelson |
| 6,969,390 B2 | 11/2005 | Michelson |
| 6,989,013 B2 | 1/2006 | Pisharodi |
| 7,001,389 B1 | 2/2006 | Navarro et al. |
| 7,052,499 B2 | 5/2006 | Steger et al. |
| 7,074,221 B2 | 7/2006 | Michelson |
| 7,077,844 B2 | 7/2006 | Michelson |
| 2001/0021851 A1 | 9/2001 | Eberlein et al. |
| 2002/0045899 A1 | 4/2002 | Errico et al. |
| 2002/0058939 A1 | 5/2002 | Wagner et al. |
| 2003/0171753 A1 | 9/2003 | Collins et al. |
| 2003/0199876 A1 | 10/2003 | Brace et al. |
| 2004/0068319 A1 | 4/2004 | Cordaro |
| 2004/0106925 A1 | 6/2004 | Culbert |
| 2004/0127899 A1 | 7/2004 | Konieczynski et al. |
| 2004/0254579 A1 | 12/2004 | Buhren et al. |
| 2005/0004574 A1 | 1/2005 | Muckter |
| 2005/0027296 A1 | 2/2005 | Thramann et al. |
| 2005/0033298 A1 | 2/2005 | Hawkes et al. |
| 2005/0059970 A1 | 3/2005 | Kolb |
| 2005/0143737 A1 | 6/2005 | Pafford et al. |
| 2005/0154392 A1 | 7/2005 | Medoff et al. |
| 2005/0192577 A1 | 9/2005 | Mosca et al. |
| 2005/0192578 A1 * | 9/2005 | Horst ............................... 606/69 |
| 2005/0228386 A1 | 10/2005 | Ziolo et al. |
| 2005/0277937 A1 | 12/2005 | Leung et al. |
| 2005/0283152 A1 | 12/2005 | Lindemann et al. |
| 2006/0004362 A1 | 1/2006 | Patterson et al. |
| 2006/0009770 A1 | 1/2006 | Speirs et al. |
| 2006/0116678 A1 | 6/2006 | Impellizzeri |
| 2006/0122602 A1 | 6/2006 | Konieczynski et al. |
| 2006/0149249 A1 | 7/2006 | Mathoulin et al. |
| 2006/0149256 A1 | 7/2006 | Wagner et al. |
| 2006/0161157 A1 | 7/2006 | Mosca et al. |
| 2006/0235399 A1 | 10/2006 | Carls et al. |
| 2008/0177330 A1 | 7/2008 | Ralph et al. |
| 2008/0234750 A1 | 9/2008 | Woods et al. |
| 2008/0234751 A1 * | 9/2008 | McClintock .................. 606/291 |
| 2008/0243192 A1 * | 10/2008 | Jacene et al. .................. 606/290 |

FOREIGN PATENT DOCUMENTS

| | | |
|---|---|---|
| WO | 9416634 A1 | 8/1994 |
| WO | 2005018472 A1 | 3/2005 |
| WO | 2007014192 A2 | 2/2007 |

OTHER PUBLICATIONS

Extended European Search Report for Application No. 08730817.7 dated Mar. 23, 2012.

Grubb et al., "Biomechanical Evaluation of Anterior Cervical Spine Stabilization," Spine, vol. 23, 1998, pp. 886-892.

International Preliminary Report on Patentability PCT/US08/055085 dated Sep. 29, 2009.

International Search Report and Written Opinion for PCT/US08/055085 dated Aug. 21, 2008.

Law, et al., "Caudo-Cephalad Loading of Pedicle Screws: Mechanisms of Loosening and Methods of Augmentation," Spine, 1993, pp. 2438-2443.

Spivak, et al., "The Effect of Locking Fixation Screws on the Stability of Anterior Cervical Plating," Spine, vol. 24, 1999, pp. 334-338.

* cited by examiner

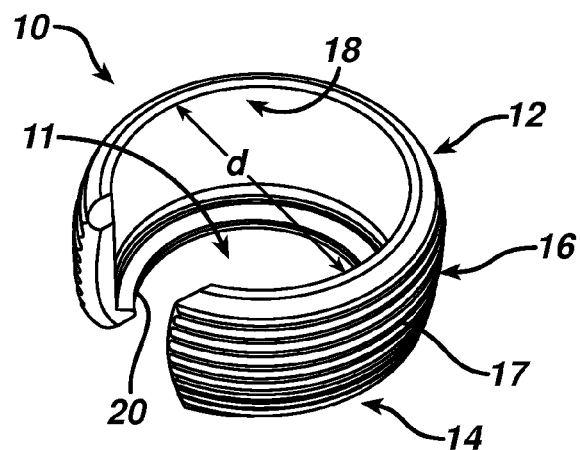
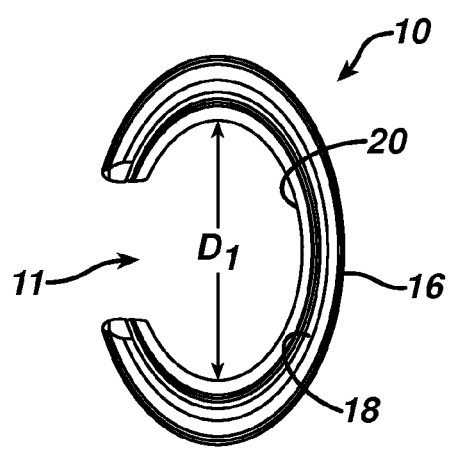
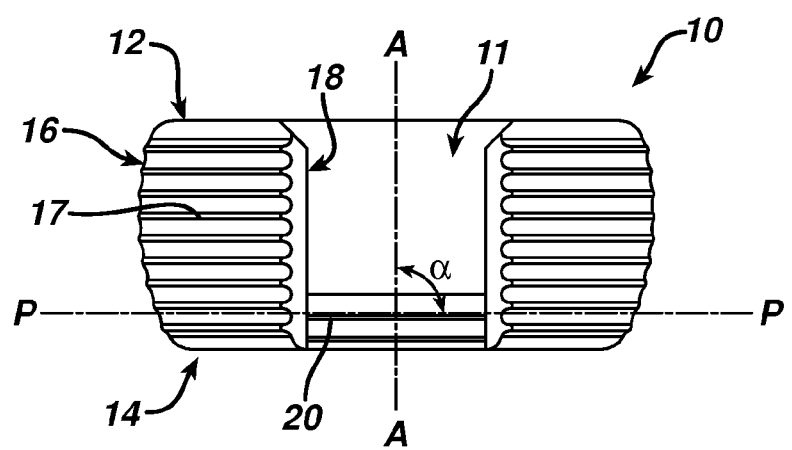

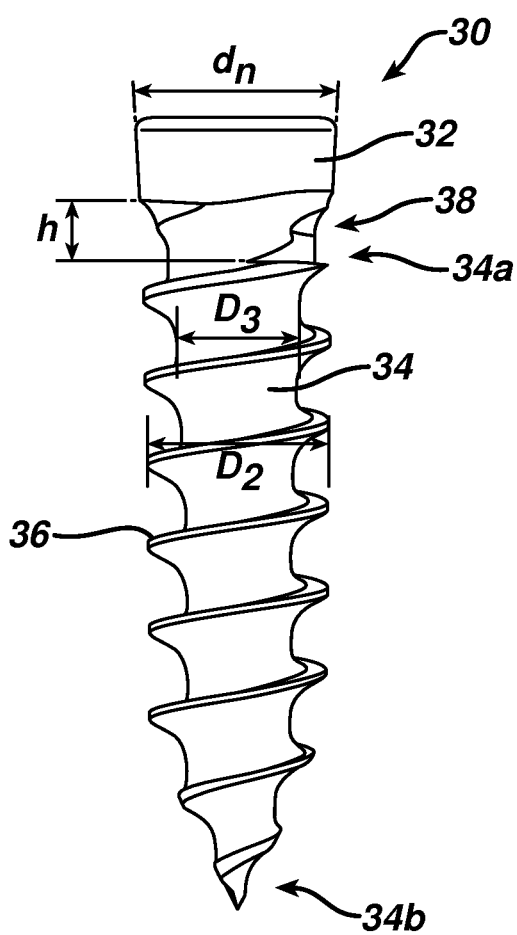
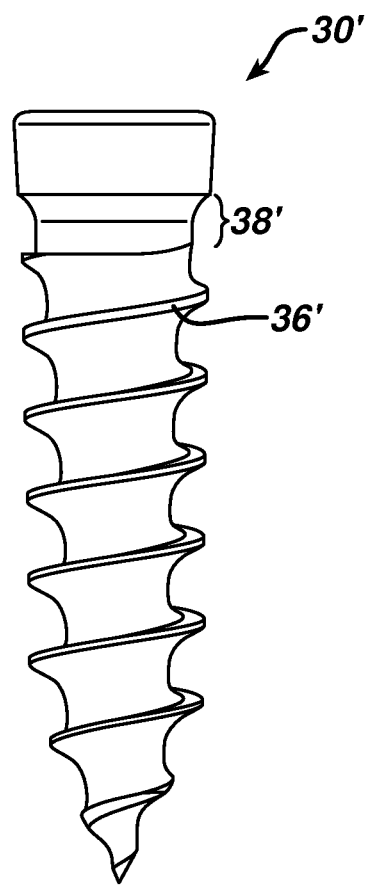
FIG. 3A
FIG. 3B

PASSIVE SCREW LOCKING MECHANISM

CROSS REFERENCE TO RELATED APPLICATIONS

This application is a continuation of U.S. application Ser. No. 11/691,760 filed on Mar. 27, 2007 and entitled "Passive Screw Locking Mechanism," which is hereby incorporated by reference in its entirety.

FIELD OF THE INVENTION

The present invention relates to bone fixation methods and devices, and in particular to a passive locking mechanism for mating a bone screw to a bone plate.

BACKGROUND OF THE INVENTION

Bone fixation devices are useful for promoting the proper healing of injured or damaged vertebral bone segments caused by trauma, tumor growth, or degenerative disc disease. These external fixation devices immobilize the injured bone segments to ensure the proper growth of new osseous tissue between the damaged segments. External bone fixation devices such as these often include internal bracing and instrumentation to stabilize the spinal column to facilitate the efficient healing of the damaged area without deformity or instability, while minimizing any immobilization and post-operative care of the patient.

One type of external bone fixation device is an osteosynthesis plate, more commonly referred to as a bone plate, that can be used to immobilize adjacent skeletal parts such as vertebral bones. Typically, the fixation plate is a rigid metal or polymeric plate positioned to span bones or bone segments that require immobilization with respect to one another. The plate is fastened to the respective bones, using anchors such as bone screws, so that the plate remains in contact with the bones and fixes them in a desired position. Anterior cervical plates, for instance, can be useful in providing the mechanical support necessary to keep vertebral bodies in proper position and bridge a weakened or diseased area such as when a disc, vertebral body or spinal fragment has been removed. These anterior cervical plates usually include a rigid bone plate having a plurality of screw openings. The openings are either holes or slots that allow for freedom of screw movement. The bone plate is placed against the damaged vertebral bodies and bone screws are used to secure the bone plate to the spine, usually with the bone screws being driven into the vertebral bodies.

While current bone plates and bone screws are effective, unintentional loosening of the screws can reduce the effectiveness of an anterior construct and can result in erosion and irritation of the esophagus. Several techniques have been developed to prevent screw back-out, however many current techniques require the use of a second locking mechanism that is applied to the bone screw or plate. This can complicate the procedure, as it requires the use of additional tools as well as proper placement of the additional locking mechanism. Other existing techniques require precise alignment of the bone screw with the thru-hole in the bone plate, thereby limiting the insertion trajectory of the bone screw.

Accordingly, there remains a need for improved methods and devices for locking a bone screw to a bone plate.

SUMMARY OF THE INVENTION

Methods and devices are provided for passively locking a bone screw to a bone plate. In one embodiment, a locking plate apparatus is provided and includes a body having a thru-hole formed therein and an annular feature formed on an internal surface of the thru-hole. The apparatus can also include a bone screw having a threaded shaft adapted to engage the annular feature upon insertion of the threaded shaft through the thru-hole.

The body can have a variety of configurations, for example the body can be a bone plate having the thru-hole formed therein. In another embodiment, the body can be a bushing having the thru-hole formed therein. The bushing can be adapted to be seated within a thru-hole in a bone plate. In certain exemplary embodiments, the bushing is split, e.g., c-shaped. The bushing can also include a radial exterior surface sized to permit polyaxial rotation of the bushing within a thru-hole in a bone plate.

The bone screw can also have a variety of configurations, but in an exemplary embodiment the bone screw includes a head that is formed on a proximal end of a threaded shaft and that is adapted to be at least partially seated within the thru-hole in the body. The threaded shaft can have an outer or major diameter that is greater than an inner diameter of the annular feature, and an inner or minor diameter that is less than an inner diameter of the annular feature, such that the annular feature engages the threads when the bone screw is inserted through the thru-hole. The bone screw can also include an annular groove formed on or adjacent to the head and/or the threaded shaft for seating the annular feature. The bone screw can also have other features. For example, the head of the bone screw can be tapered for seating within a corresponding tapered portion of the thru-hole.

The annular feature can also have a variety of configurations. The annular feature can be, for example, an annular flange disposed around an inner surface of the thru-hole, or a plurality of flanges or tabs spaced annularly around an inner surface of the thru-hole. In an exemplary embodiment, the annular feature resides within a single plane, which can optionally be perpendicular to a longitudinal axis of the thru-hole. In use, the annular feature can be sized to engage threads on the bone screw and to retain the bone screw within the body.

In another embodiment, a method for locking a bone screw within a plate is provided and includes positioning a body having a thru-hole on a bone surface. The thru-hole can include an annular feature formed therein. The method can also include inserting a bone screw through the thru-hole in the body and into bone. Threads on the bone screw can engage the annular feature as the bone screw is inserted through the thru-hole. In an exemplary embodiment, the annular feature resides in a single plane such that the bone screw can be inserted through the thru-hole at various insertion angles relative to an axis of the thru-hole. Once implanted, the annular feature will retain the bone screw within the thru-hole thereby preventing back-out.

BRIEF DESCRIPTION OF THE DRAWINGS

The invention will be more fully understood from the following detailed description taken in conjunction with the accompanying drawings, in which:

FIG. 1A is a perspective view of one embodiment of a bushing having an annular feature formed therein;

FIG. 1B is a top view of the bushing of FIG. 1A;

FIG. 1C is a side cross-sectional view of the bushing of FIG. 1A;

FIG. 3A is a side view of one embodiment of a bone screw;

FIG. 3B is a side view of another embodiment of a bone screw;

DETAILED DESCRIPTION OF THE INVENTION

Figure 2A:
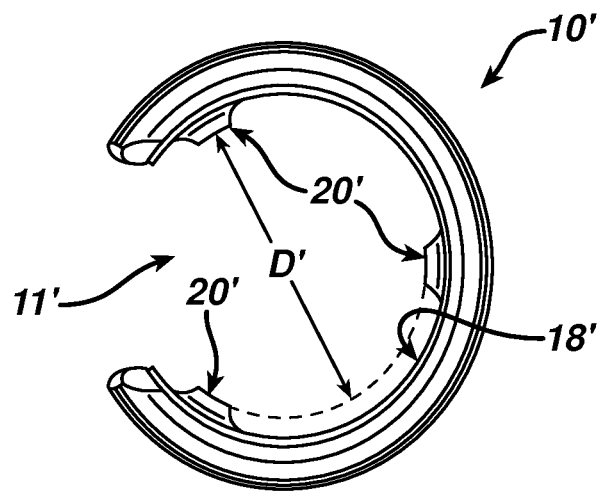
FIG. 2A is a top view of another embodiment of a bushing having an annular feature formed therein.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for passively locking a bone screw within a bone plate. In particular, the methods and devices allow a bone screw to be locked within a thru-hole in a bone plate without requiring any additional locking steps. In an exemplary embodiment, an annular feature is provided in a thru-hole of a body, such as a bone plate or a bushing that is disposed within a thru-hole of a bone plate, for engaging a bone screw. The annular feature can be configured such that it allows the bone screw to be inserted through the thru-hole at various insertion angles while still being effective to prevent back-out of the bone screw, thereby locking the screw to the plate. A person skilled in the art will appreciate that, while the invention is described as not requiring any additional locking steps, various locking mechanisms known in the art can be used in combination with the passive locking feature disclosed herein.

As indicated above, in one embodiment an annular feature is provided in a thru-hole of a bone plate, or in a bushing that is disposed within a thru-hole of a bone plate, for engaging a bone screw. FIGS. 1A-1C illustrate one exemplary embodiment of an annular feature 20 that is formed around an inner surface 18 of a thru-bore 11 in a bushing 10. The particular configuration of the bushing 10 can vary, but the illustrated bushing 10 is a split bushing that is generally C-shaped. Other slot or cut-out configurations can be used to allow radial expansion of the bushing, or alternatively the bushing can be ring-shaped. The illustrated bushing 10 generally includes a first or proximal end 12 that is configured to lie adjacent to a proximal surface of a bone plate, and a second or distal end 14 that is configured to lie adjacent to a distal, bone-contacting surface of a bone plate, as will be discussed in more detail below. An outer surface 16 of the bushing 10 can be sized and shaped to match the inner surface of the thru-hole in a bone plate. As shown in FIG. 1A, the outer surface of the bushing has a generally convex spherical shape extending between the first and second ends 12, 14 such that the bushing 10 can be seated within a thru-hole having a generally concave spherical inner surface extending between first and second surfaces of the bone plate. This will allow the bushing 10 to move polyaxially relative to the plate. The outer surface 16 of the bushing 10 can also include surface features formed thereon to facilitate frictional engagement with the thru-hole in a bone plate. FIGS. 1A and 1C illustrate ridges 17 extending radially around the bushing 10. A variety of other surface features or textures can be used to facilitate engagement between the bushing 10 and a thru-hole, or alternatively the bushing 10 can have a smooth outer surface. The inner surface 18 of the bushing 10 can also have a variety of configurations, but in an exemplary embodiment the inner surface 18 has a diameter d that decreases from the proximal end 12 to the distal end 14 such that the thru-bore 11 is tapered.

Continuing to refer to FIGS. 1A-1C, the annular feature 20 can have a variety of configurations but in the illustrated embodiment the annular feature 20 is in the form of an annular flange or protrusion that extends radially around the inner surface 18 of the bushing 10. The diameter $D_1$ of the annular feature 20 can vary, but it is preferably sized to engage the threads of the bone screw to prevent screw back-out once the bone screw is implanted. In an exemplary embodiment, the annular feature 20 has a diameter $D_1$ that is greater than a major or outer diameter of the threads of a bone screw inserted therethrough, and that is less than a minor or inner diameter of the threads of a bone screw inserted therethrough (i.e., the diameter of the shank). The inner diameter $D_1$ of the annular feature 20 is also preferably smaller than the smallest outer diameter of a head of the bone screw so as to prevent the head of the bone screw from passing therethrough. Exemplary bone screws will be discussed in more detail below with respect to FIGS. 3A and 3B.

The particular location of the annular feature 20 within the thru-hole 11 of the bushing 10 can also vary. In the illustrated embodiment the annular feature 20 is positioned adjacent to a distal end of the thru-hole 11, i.e., adjacent to the distal-most end 14 of the bushing 10. This configuration will allow the annular feature to engage the bone screw at a location between the shank and the head, as will be discussed in more detail below. A person skilled in the art will appreciate that the annular feature can be located at any portion in the bushing, and that the particular location can vary depending on the configuration of the bone screw. Moreover, while a bushing is shown, the annular feature can be formed in a thru-hole in a bone plate such that the bone plate has a thru-hole with the same configuration as thru-hole 11.

As further shown in FIGS. 1A-1C, the annular feature 20 can also reside in a single plane P such that the annular feature 20 is non-helical or non-threaded. The angle of the plane P relative to a central axis A of the thru-hole 11 can vary. For example, the annular feature 20 can reside in a plane P that extends at an angle α that is greater than or less than 90° relative to the central axis A of the thru-hole 11. In the illustrated embodiment, the annular feature 20 resides in a plane P that is perpendicular to the central axis A of the thru-hole 11 such that the plane P extends at an angle α of 90° relative to the central axis A. In use, the planar configuration of the annular feature 20 will allow a bone screw to be inserted at various trajectories or insertion angles relative to the thru-hole 11, as the annular feature 20 will extend between the threads without requiring the tight constraints and proper alignment that are necessary with a thread-on-thread connection. A person skilled in the art will appreciate that the thru-hole 11 can, however, include a partial thread formed therein, in addition to the annular feature, for positioning the bone screw at a predetermined trajectory relative to the thru-hole. Moreover, while only one annular feature is shown, the thru-hole 11 can include multiple annular features residing in separate planes.

Figure 2B:
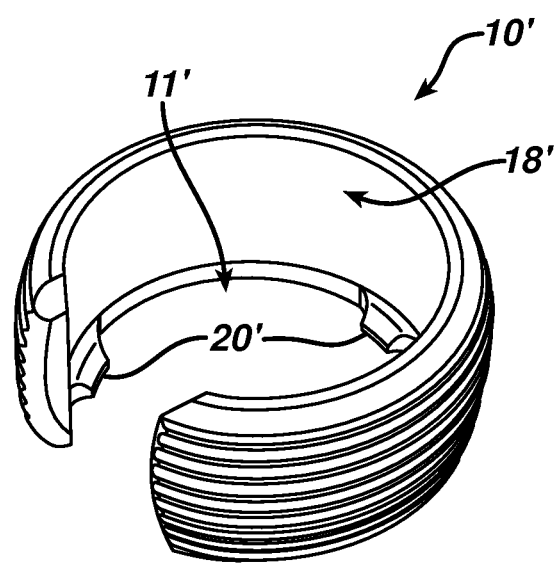
FIG. 2B is a perspective view of the bushing of FIG. 2A.

FIGS. 2A-2B illustrate yet another embodiment of an annular feature 20' that is configured to lock a bone screw within a thru-hole in a plate. As with the embodiment shown in FIGS. 1A-1C, the annular feature 20' is formed within a thru-hole 11' of a bushing 10' and resides in a single plane. The annular feature 20' also similarly has an inner diameter $D_1'$ that is greater than a major diameter of the threads on a bone screw, but less than a minor diameter of the threads on the bone screw, as will be discussed in more detail below. In this embodiment, however, rather than extending around an entire inner surface 18' of the bushing 10', the annular feature 20' is in the form of multiple protrusions or flanges that are positioned annularly around an inner surface 18' of the bushing 10'. FIGS. 2A-2B illustrate three protrusions spaced radially around the inner surface 18' of the bushing 10'.

As indicated above, the annular feature can be configured to engage a bone screw to lock the bone screw to a bone plate. FIG. 3A illustrates one exemplary embodiment of a bone screw 30 for use with the bushings 10, 10' shown in FIGS. 1A-2B. In general, the bone screw 30 includes a head 32 and a shank 34 extending distally therefrom. The head 32 can be sized to be at least partially received within a thru-hole 11, 11' in the bushing 10, 10', or within a thru-hole in a bone plate. In an exemplary embodiment, the head 32 has a diameter $d_h$ that is greater than the inner diameter $D_1$, $D_1'$ of the annular feature 20, 20' such that the annular feature 20, 20' prevents passage of the head 32 through the thru-hole 11, 11'. The shank 34 includes threads 36 formed thereon and extending between proximal and distal ends 34a, 34b of the shank 34. The shape of the tip of bone screw 30 can vary, and the tip can be self-drilling or self-tapping if desired. In order to allow the annular feature 20, 20' to lock the bone screw 30 to a bone plate, the threads 36 on the shank 34 can have a major diameter $D_2$ that is greater than the inner diameter $D_1$, $D_1'$ of the annular feature 20, 20', and a minor diameter $D_3$, i.e., the diameter of the shank, that is less than the inner diameter $D_1$, $D_1'$ of the annular feature 20, 20'. This will allow the annular feature 20, 20' to extend between the threads 36 as the bone screw 30 is threaded therethrough. As previously indicated, since the annular feature 20, 20' resides in a single plane, the bone screw 30 can be inserted at various trajectories or insertion angles relative to the annular feature 20, 20', thus allowing easy insertion of the bone screw 30 into bone.

As further shown in FIG. 3A, the bone screw 30 can include an annular groove 38 formed on or adjacent to the head 32 and/or the proximal end 34a of the shank 34. In the illustrated embodiment, the groove 38 is located between the proximal end of the shank 34 and the head 32. A person skilled in the art will appreciate that in describing the groove as being formed "between" the head 32 and the shank 34, the groove can necessarily be formed on only one of the head 32 and the shank 34, or on a portion of both the head 32 and the shank 34. The threads 36 on the shank 34 can also continue into the groove 38 and terminate at the head 32, as shown in FIG. 3A, or they can terminate prior to the groove. FIG. 3B illustrates a bone screw 30' having threads 36' that terminate prior to a groove 38' 3B. In use, the annular groove 38 is configured to seat the annular feature 20, 20' on the bushing (or on a bone plate) once the bone screw 30 is threaded therethrough, as will be discussed in more detail below. In an exemplary embodiment, the annular groove 30 has a height h that is greater than a height of the annular feature 20, 20'. This will allow the bone screw 30 to be fully threaded into bone without interference from the annular feature 20, 20'. A person skilled in the art will appreciate that the bone screw can have a variety of configurations, and that various bone screws known in the art can be used.

Figure 4:
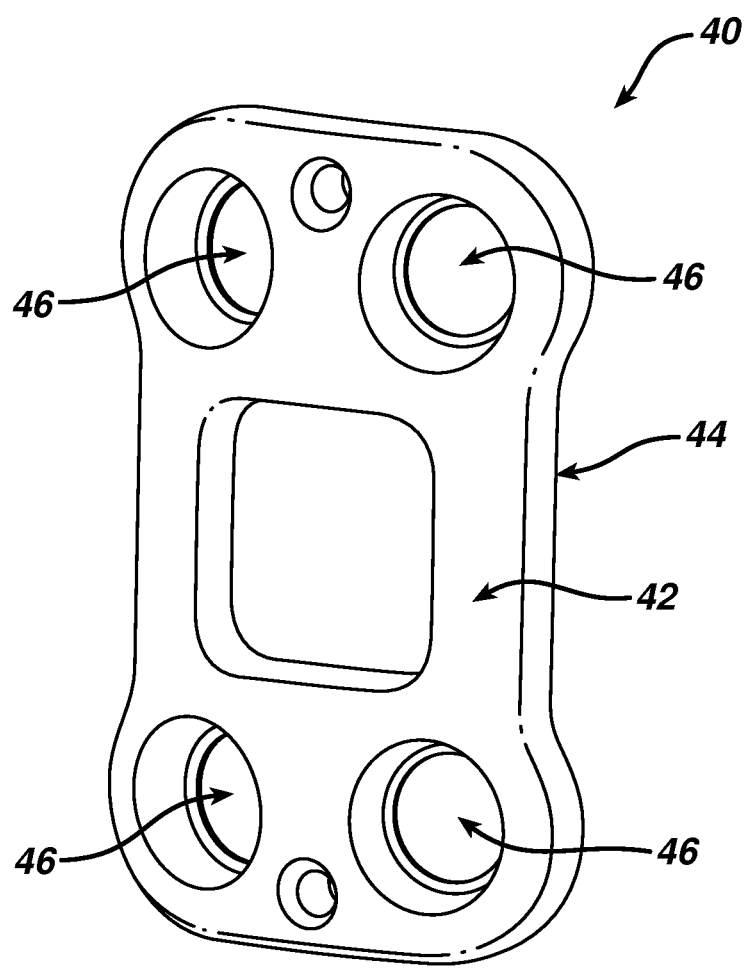
FIG. 4 is a top view of one embodiment of a bone plate.

FIG. 4 illustrates one exemplary embodiment of a bone plate 40 that can be used with the bushings 10, 10' of FIGS. 1A-2B and with the bone screws 30, 30' of FIGS. 3A and 3B. As shown, the bone plate 40 has a generally planar configuration with a first, superior surface 42 and a second, inferior bone-contacting surface 44. The plate 40 can include any number of thru-holes formed therein and extending between the superior and inferior surfaces 42, 44. In the illustrated embodiment, the plate 40 includes four thru-holes 46 formed therein for receiving four bone screws. The plate 40 can also include additional features to facilitate use of the implant. In this embodiment, each thru-hole 46 is sized and shaped to seat a bushing therein such that, when a bone screw is inserted through the bushing and into bone, an interference fit is created between the head of the bone screw, the bushing, and the thru-hole 46 in the plate 40.

Figure 5:
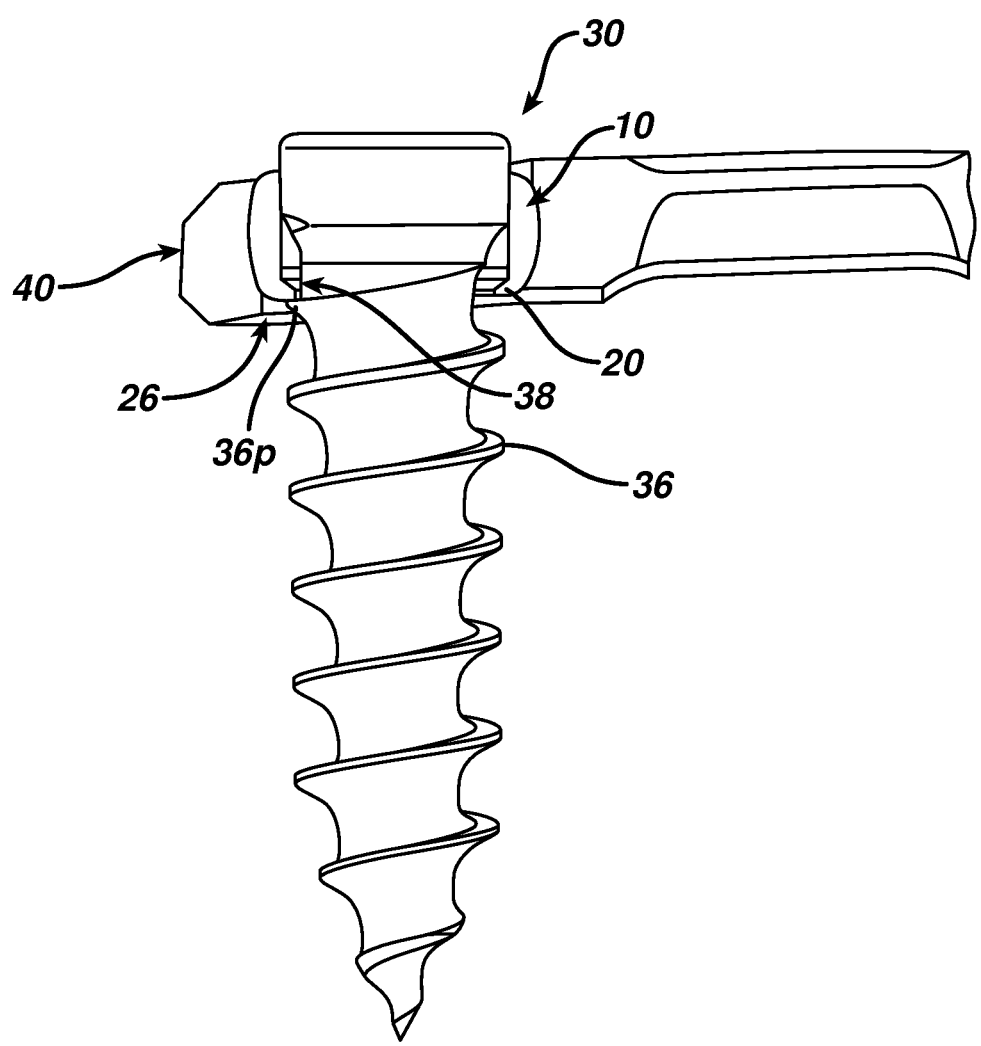
FIG. 5 is a side cross-sectional view of the bone screw of FIG. 3A disposed within the bushing of FIG. 1A, which is seated in a thru-hole of the bone plate of FIG. 4.
Figure 6:
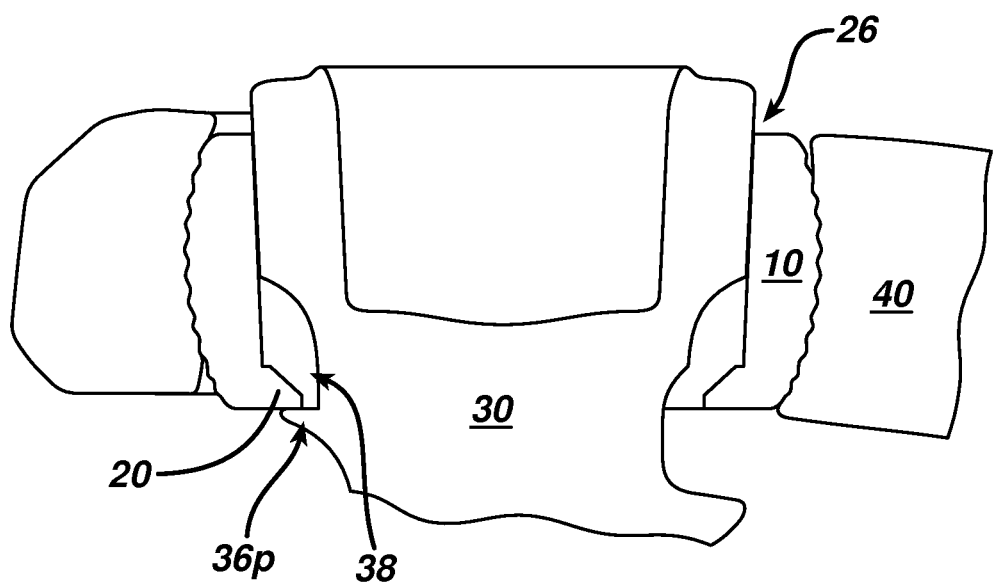
FIG. 6 is an illustration showing the bone screw, bushing, and bone plate of FIG. 5 in use in bone.

In use, the annular feature will lock the bone screw to the plate. In particular, a bushing can be disposed within a thru-hole in a plate (or alternatively the annular feature can be formed directly in the thru-hole in the plate). The plate can be positioned against a bone surface, such as against a vertebra in a spinal column. Once the bone is prepared, e.g., by drilling, tapping, etc., a bone screw can be passed through the thru-hole in the bushing (or the thru-hole in the plate where the annular feature is formed in the plate) and threaded into bone. FIGS. 5 and 6 illustrate the bone screw 30 of FIG. 3A disposed through the bushing 10 of FIGS. 1A-1C, which is seated within a thru-hole 26 in the plate 40 of FIG. 4. As shown, the annular feature 20 is disposed within the annular groove 38 formed around the bone screw 30 such that the annular feature 20 will abut the proximal-most surface 36p of the thread 36 on the bone screw 30 to prevent the screw 30 from backing out of the plate 40. Thus, in order to remove the bone screw 30 from the bone plate 40, the screw 30 will need to be unthreaded. The annular feature 20 is therefore effective to passively lock the bone screw 30 to the plate 40, as additional locking mechanisms are not required.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A locking plate apparatus, comprising:
   a bushing configured to be seated within a thru-hole in a bone plate, the bushing having a thru-hole formed therein and an annular feature formed on an internal surface of the thru-hole, the annular feature residing in a single plane and having an inner diameter;
   a bone plate having a thru-hole formed therein and sized to seat the bushing; and
   a bone screw having a threaded shaft with threads having a major diameter that is greater than the inner diameter of the annular feature such that the annular feature extends between the threads on the threaded shaft as the threaded shaft is inserted through the thru-hole of the bushing.

2. The apparatus of claim 1, wherein the bushing is c-shaped.

3. The apparatus of claim 1, wherein the bushing includes a radial exterior surface sized to permit polyaxial rotation of the bushing within the thru-hole in the bone plate.

4. The apparatus of claim 1, wherein the annular feature is configured to abut a proximal-most surface of the threads on the threaded shaft when the threaded shaft is threaded through the thru-hole in the bushing.

5. The apparatus of claim 4, further comprising an annular groove formed between a head of the bone screw and the threaded shaft of the bone screw, the annular groove seating the annular feature when at least a portion of the head of the bone screw is seated within the bushing.

6. The apparatus of claim 1, wherein the bone screw includes a head formed on a proximal end of the threaded shaft and adapted to be at least partially seated within the thru-hole in the bushing.

7. The apparatus of claim 6, wherein the head is tapered and at least a portion of the thru-hole in the bushing is tapered for seating the head.

8. The apparatus of claim 1, wherein the annular feature comprises an annular flange disposed around an inner surface of the thru-hole in the bushing.

9. The apparatus of claim 1, wherein the annular feature comprises a plurality of tabs spaced annularly around an inner surface of the thru-hole in the bushing.

10. A screw locking device, comprising:
- a split bushing configured to be seated within a thru-hole in a bone plate, the bushing including an annular feature formed on an internal surface thereof and residing only in a plane perpendicular to an axis of a thru-hole formed in the bushing;
- a bone screw having a threaded shank configured to be passed through the split bushing for engaging bone and a head configured to be at least partially disposed within the split bushing, the annular feature being configured to abut a proximal-most surface of threads on the threaded shank to retain the bone screw within the split bushing; and
- a plate having a thru-hole formed therein that receives the split bushing.

11. The device of claim 10, wherein the annular feature retains the bone screw within the bushing using an interference fit.

12. The device of claim 10, wherein the annular feature is positioned to engage an annular groove formed between the head and the threaded shank of the bone screw.

13. The device of claim 10, wherein the threads have a major diameter that is greater than an inner diameter of the annular feature, and the threaded shank has a minor diameter that is less than an inner diameter of the annular feature.

14. The device of claim 10, wherein the annular feature is configured to engage the threads on the threaded shank.

15. The device of claim 10, wherein the annular feature comprises an annular flange disposed around an inner surface of the thru-hole in the split bushing.

16. The device of claim 10, wherein the annular feature comprises a plurality of tabs spaced annularly around an inner surface of the thru-hole in the split bushing.

\* \* \* \* \*